United States Patent [19]

Wong et al.

[11] 4,327,080
[45] Apr. 27, 1982

[54] NOVEL BENDROFLUMETHIAZIDE FORMULATIONS AND METHOD

[75] Inventors: Thomas M. Wong, North Brunswick; Mahendra R. Patel, East Brunswick, both of N.J.

[73] Assignee: E. R. Squibb & Sons, Inc., Princeton, N.J.

[21] Appl. No.: 282,359

[22] Filed: Jul. 13, 1981

[51] Int. Cl.³ .................... A61K 9/20; A61K 31/79; A61K 47/00
[52] U.S. Cl. ................. 424/80; 424/246; 424/362
[58] Field of Search ................. 424/80, 246, 362

[56] References Cited

U.S. PATENT DOCUMENTS

| | | | |
|---|---|---|---|
| 2,820,741 | 1/1958 | Endicott et al. | 424/80 |
| 2,918,411 | 12/1959 | Hill | 424/80 |
| 3,102,845 | 9/1963 | Fennell | 424/80 |
| 3,136,692 | 6/1964 | Bandelin | 424/80 |
| 3,257,277 | 6/1966 | Hwang | 424/80 |
| 3,265,573 | 8/1966 | Goldberg . | |
| 3,632,778 | 1/1972 | Sheth et al. | 424/80 |
| 3,673,163 | 6/1972 | Walkling | 424/80 |
| 3,920,809 | 11/1975 | Thakkar | 424/80 |
| 3,932,615 | 1/1976 | Ito et al. | 424/80 |
| 4,143,129 | 3/1979 | Marsden | 424/80 |
| 4,195,078 | 3/1980 | Conine | 424/80 |

FOREIGN PATENT DOCUMENTS 7611731 5/1977 Netherlands .
1509778 5/1978 United Kingdom .

OTHER PUBLICATIONS

Rubenstein, M. H., Drug Dev. Ind. Pharm. 1977, 3(5), 439-450, The Effect of Excipient Solubility on the in vitro and in vivo Properties of Bendrofluazide Tablets 5 mg.
Rubenstein, M. H., Pharm. Acta. Helv. 1977, 52(1-2), 5-10, The Effect of Granule Size on the in vitro and in vivo Properties of Bendrofluazide Tablets 5 mg.
Beermann, B., Clin. Pharmacol. Ther. 1977, 22(4), 385-388.
Beermann, B., Acta. Med. Scand. 1978, 204(4), 291-293.
Corrigan, Ol et al., Int. J. Pharm. 1979, 4(1), 67-74.

*Primary Examiner*—Shep K. Rose
*Attorney, Agent, or Firm*—Lawrence S. Levinson; Burton Rodney

[57] ABSTRACT

New bendroflumethiazide formulations in solid form are provided which are characterized by excellent disintegration and dissolution capabilities even after long periods of storage. The new bendroflumethiazide formulations, for example, in the form of tablets, are formed of one or more excipients and a dry granulation containing one or more fillers, such as lactose and starch, and a preformed partial coprecipitate of bendroflumethiazide and a wetting agent therefor, such as polyvinyl pyrrolidone which converts the bendroflumethiazide into a more hydrophilic form.

24 Claims, No Drawings

NOVEL BENDROFLUMETHIAZIDE FORMULATIONS AND METHOD

FIELD OF THE INVENTION

The present invention relates to bendroflumethiazide formulations, in solid form, especially tablets, which have improved disintegration properties and dissolution properties even after storage for long periods of time, and to a method for preparing such formulations.

BACKGROUND OF THE INVENTION

Bendroflumethiazide (the generic name for 3-benzyl-3,4-dihydro-7-sulfamoyl-6-trifluoromethyl-1,2,4-benzothiadiazine 1,1-dioxide) is known as a diuretic and antihypertensive agent as disclosed in U.S. Pat. No. 3,265,573. However, bendroflumethiazide has a dissolution problem due to its hydrophobic nature and low solubility. Its in vivo bioavailability is compromised due to its poor dissolution from tablets. Reduction in particle size and selection of a fast dissolving polymorphic form improves its dissolution but not to a desired acceptable level.

When formulated as a tablet, bendroflumethiazide is usually in admixture with gum acacia which serves as a binder, corn starch which serves as a disintegrant, together with a lactose diluent, lubricant and water-soluble dyes.

The prior art bendroflumethiazide tablets are prepared by first dissolving part of the gum acacia binder and water-soluble dyes in water, adding lactose to the resulting solution, drying the mixture, reducing the resulting particles to fine granules, and then mixing such granules with the bendroflumethiazide, cornstarch and remainder of the gum acacia, and compressing the mixture into tablets. Such tablet formulations disintegrate in water after about 9 minutes and have good dissolution properties upon aging. However, tablet formulations which have improved disintegration properties and dissolution properties and are faster and cheaper to manufacture would still be most desirable.

DESCRIPTION OF THE INVENTION

In accordance with the present invention, a unique bendroflumethiazide formulation in solid oral dosage form, especially in tablet form, is provided wherein gum acacia is not employed and therefore water is not mixed with any of the formulation ingredients. Accordingly, the bendroflumethiazide formulation of the invention is faster and less expensive to manufacture than prior art formulations, and is more stable, and has faster disintegration and dissolution times than prior art formulations. The bioavailability of bendroflumethiazide from the above type of dosage form is at a maximum equivalent to a solution form. In addition, since water is not employed in the formulation of the invention, the risk of drug degradation due to water is eliminated.

The solid bendroflumethiazide formulation of the invention contains one or more excipients substantially uniformly mixed with a dry granulation including one or more fillers and a preformed partial coprecipitate formed of bendroflumethiazide and a wetting or granulating agent therefor for converting the bendroflumethiazide into a more hydrophilic form.

In addition, the bendroflumethiazide formulation of the invention may contain an anti-hypertensive agent and/or a beta-blocking agent (which itself may or may not be an anti-hypertensive agent), such as nadolol, propranolol, or timolol, as well as anti-hypertensive drugs, such as captopril.

Further, in accordance with the present invention, a method is provided for preparing the new hydrophilic bendroflumethiazide formulation of the invention, which method includes the steps of forming a wet granulation of bendroflumethiazide including one or more fillers, such as lactose, starch and/or microcrystalline cellulose; wetting or granulating agent for bendroflumethiazide, such as polyvinyl pyrrolidone; and a solvent for bendroflumethiazide, such as ethanol; drying the wet granulation, for example, by use of fluid-bed or tray dryers causing the solvent to evaporate and the bendroflumethiazide and wetting agent to form a partial coprecipitate, thereby forming a dry granulation, reducing the average particle size of the dry granulation to below about 500 microns, and mixing the dry granulation with excipients to form the solid bendroflumethiazide formulation of the invention.

The afore-described wet granulation is formed by mixing bendroflumethiazide and fillers to form a bendroflumethiazide composition, dissolving wetting or granulating agent in the solvent to form a granulating mixture, and mixing the granulating mixture with the bendroflumethiazide composition.

Where it is desired to include an anti-hypertensive agent or a beta-blocking agent in the bendroflumethiazide formulation of the invention, the anti-hypertensive agent or beta-blocking agent will be separately granulated with filler and precompacted and mixed with the dry bendroflumethiazide formulation before mixing with the excipients.

By means of the above method, dissolution of bendroflumethiazide from the oral dosage form is substantially improved. It is believed that the improved dissolution of bendroflumethiazide is achieved by means of the wet granulation technique using the wetting agent and solvent described above which aids in wetting, dispersing and partially forming coprecipitates of the bendroflumethiazide and wetting or granulating agent.

In carrying out the method of the invention, in forming the wet granulation, the bendroflumethiazide will first be mixed with one or more fillers, such as starch (of the gelatinized type such as Sta Rx brand starch made by Colorcon, Inc.), lactose, microcrystalline cellulose, dicalcium phosphate, sucrose, calcium sulphate or sodium starch glycolate or mixtures thereof, with a mixture of lactose and starch being preferred, in a weight ratio of bendroflumethiazide:filler of within the range of from about 1:40 to about 1:8 and preferably from about 1:30 to about 1:15, to form the bendroflumethiazide composition.

The bendroflumethiazide composition is mixed with a mixture of the wetting agent and solvent employing a weight ratio of bendroflumethiazide to wetting agent of within the range of from about 0.5:1 to about 5:1 and preferably from about 0.7:1 to about 1.5:1, and a weight to volume ratio of bendroflumethiazide to solvent of within the range of from about 1:15 to about 1:45, and preferably from about 1:20 to about 1:30. The wetting agent is employed in a weight to volume ratio to the solvent of within the range of from about 1:15 to about 1:45, and preferably from about 1:20 to about 1:30.

Examples of wetting or granulating agents for bendroflumethiazide suitable for use herein include, but are not limited to, polyvinyl pyrrolidone, hydroxypropylmethyl cellulose, hydroxypropyl cellulose or methyl cellulose, with polyvinyl pyrrolidone being preferred.

Examples of solvent for bendroflumethiazide suitable for use herein include, but are not limited to, ethanol, methylene chloride, isopropanol, methanol, acetone or water, with ethanol being preferred.

The excipients which may be included in the bendroflumethiazide formulation of the invention include one or more disintegrants, such as sodium carboxymethyl starch, modified cellulose, cross-linked polyvinyl pyrrolidone, or corn starch, with sodium carboxymethyl starch being preferred, in an amount within the range of from about 0 to about 10% and preferably from about 1 to about 6% by weight, fillers such as any of those mentioned above, with microcrystalline cellulose being preferred, in an amount within the range of from about 0 to about 80% and preferably from about 10 to about 50%, optional colorants in an amount of from about 0 to about 6% and preferably from about 0.5 to about 2%.

The excipients may also include a tabletting lubricant which may comprise conventional type tabletting lubricants, such as magnesium stearate, cornstarch, talc, stearic acid or mixtures thereof with magnesium stearate being preferred, present in an amount within the range of from about 0 to about 3% and preferably from about 0.1 to about 2% by weight. All of the above percents are based upon the weight of the total bendroflumethiazide formulation.

Preferred table formulations in accordance with the present invention are set out below.

| Ingredient | Most Preferred % by Weight |
| --- | --- |
| Bendroflumethiazide | 2.5 to 10 |
| Wetting agent (preferably polyvinyl pyrrolidone) | 2 to 6 |
| Fillers (preferably Lactose | 20 to 80 |
| Starch (gelatinized)) | 10 to 30 |
| Excipients Disintegrant (preferably Sodium carboxymethyl starch and/or | 1 to 6 |
| Microcrystalline cellulose) | 10 to 50 |
| Lubricant (preferably magnesium stearate) | 0.1 to 2 |
| Color | 0 to 1.5 |
| Nadolol | 11 to 36 |

The solid bendroflumethiazide formulation of the invention may comprise a tablet, capsule, pill, powder and preferably, a tablet which may take any conventional shape or size, such as square, round, oblong, pill-shape and the like. These solid forms may contain from about 0.01 to about 0.2 mg bendroflumethiazide per kg of body weight and may be formulated in dosages of 1–20 mg amounts.

Even in the case of the high dosage forms, the solid formulations of the invention will quickly disintegrate in water after only 1 to 5 minutes and will dissolve to 90% in 0.1 HCl within 20 minutes.

An anti-hypertensive compound or beta blocker, such as nadolol, may be present in amounts of from about 0.5 to about 2 mg per kg of body weight and may be formulated (with the bendroflumethiazide) in dosages of 20 to 160 mg amounts.

The following Examples represent preferred embodiments of the present invention.

EXAMPLE 1

A bendroflumethiazide tablet having the following composition is prepared as described below.

| Composition | Amount Parts by Weight |
| --- | --- |
| Bendroflumethiazide | 2.5 |
| Polyvinyl pyrrolidone | 2.5 |
| Lactose, Fast Flo (Foremost) | 40 |
| Pregelatinized starch (StaRx-1500 Starch, USP) | 20 |
| Microcrystalline cellulose (Avicel PH 101, NF) | 33 |
| Sodium carboxymethyl starch (Explotab) | 2 |
| F.D.C. Green Lake Blend | 1 |
| Magnesium Stearate, USP | 0.3 |

A wet granulation of bendroflumethiazide is formed as follows. Bendroflumethiazide; lactose and pregelatinized starch are mixed to form a bendroflumethiazide composition.

In a separate vessel, polyvinyl pyrrolidone and ethanol (in a weight to volume ratio of bendroflumethiazide to ethanol of 1:25) are mixed to form a granulating mixture.

The granulating mixture is then mixed with the bendroflumethiazide composition to form the wet granulation of bendroflumethiazide.

The wet bendroflumethiazide granulation is dried either by tray drying or fluid bed drying thereby causing the ethanol to evaporate and the bendroflumethiazide and polyvinyl pyrrolidone to form a partial coprecipitate (also referred to as a "dry granulation"). The resulting dry granulation is reduced in average particle size, by screening, to below about 500 microns and is then mixed with the microcrystalline cellulose, sodium carboxymethyl starch, magnesium stearate and color to form a solid bendroflumethiazide formulation which is compressed into bendroflumethiazide tablets.

The bendroflumethiazine tablets formed as described below allow for rapid dissolution of bendroflumethiazide therefrom. It is found that bendroflumethiazide bioavailability from these tablets, prepared using the wet granulation, is equivalent to that from solution form.

EXAMPLE 2

A bendroflumethiazide tablet having the following composition is prepared as described in Example 1.

| Composition | Amount Parts by Weight |
| --- | --- |
| Bendroflumethiazide | 5 |
| Polyvinyl pyrrolidone | 5 |
| Pregelatinized starch (StaRx-1500 Starch, USP) | 25 |
| Microcrystalline cellulose (Avicel PH 101) | 30 |
| Lactose, Fast Flo (Foremost) | 80 |
| Sodium carboxymethyl starch (Explotab) | 3 |
| Color | 1 |
| Magnesium Stearate, USP | 0.5 |

The bendroflumethiazide tablets of the above composition formed as described in Example 1 allow for rapid dissolution of bendroflumethiazide therefrom so that bioavailability of bendroflumethiazide from these tablets is equivalent to that from solution form.

EXAMPLE 3

A bendroflumethiazide tablet having the following composition is prepared as described in Example 1.

| Composition | Amount Parts by Weight |
|---|---|
| Bendroflumethiazide | 10 |
| Polyvinyl pyrrolidone | 10 |
| Pregelatinized starch (StaRx-1500 Starch, USP) | 29 |
| Microcrystalline cellulose (Avicel PH 101) | 32 |
| Lactose, Fast Flo (Foremost) | 160 |
| Sodium carboxymethyl starch (Explotab) | 5 |
| Color | 3 |
| Magnesium stearate, USP | 0.8 |

The bendroflumethiazide tablets of the above composition formed as described in Example 1 allow for rapid dissolution of bendroflumethiazide therefrom so that bioavailability of bendroflumethiazide from these tablets is equivalent to that from solution form.

EXAMPLES 4 TO 8

The following bendroflumethiazide-nadolol combination tablet formulations are prepared as described below.

| Example No. | 4 | 5 | 6 | 7 | 8 |
|---|---|---|---|---|---|
| Ratio Nadolol:Bendroflumethiazide | 160:5 | 80:5 | 40:5 | 60:5 | 120:5 |
| Ingredient | Parts by Weight | | | | |
| Bendroflumethiazide granulation* | 100 | 100 | 100 | 100 | 100 |
| Nadolol granulation** | 240 | 120 | 60 | 90 | 180 |
| Microcrystalline cellulose (Avicel PH 102,NF) | 65 | 95.5 | 58 | 75.5 | 80 |
| Sodium carboxymethyl starch (Explotab) | 13.5 | 10 | 12 | 10.5 | 12 |
| Blue #2 Nu-Pariels | 27 | 21 | 17.5 | 21 | 24 |
| Magnesium stearate | 4.5 | 3.5 | 2.5 | 3 | 4 |

*Bendroflumethiazide granulation (prepared as described in Example 1)

| Ingredient | Parts by Weight |
|---|---|
| Bendroflumethiazide | 5 |
| Polyvinyl pyrrolidone | 5 |
| Pregelatinized starch (Sta Rx-1500 Starch, U.S.P.) | 10 |
| Lactose, anhydrous | 80 |
| Ethyl alcohol (is not present in final tablet - removed during drying) | 0 |

**Nadolol granulation

| Ingredient | Parts by Weight |
|---|---|
| Nadolol | 2 parts |
| Microcrystalline cellulose (Avicel PH 102, NF) | 1 part |

Therefore, in the 160:5 microcrystalline cellulose:nadolol combination tablet (Example 4), in 240 parts of the nadolol granulation, 160 parts will be nadolol and 80 parts will be microcrystalline cellulose.

The above ingredients including bendroflumethiazide granulation and nadolol granulation and the other excipients are mixed together and compressed into tablets.

The above nadolol:bendroflumethiazide tablets are tested for comparative bioavailability against a 5 mg bendroflumethiazide solution in dogs employing the following test.

Four formulations are employed in a four-way crossover study, namely, 5 mg solution in water/ethanol (99.5:0.5 v/v) (A); 5 mg aqueous suspension (B); 5 mg reformulated tablet (C); and 5 mg bendroflumethiazide-40 mg nadolol combination tablet (D). Six female dogs each receive a single 5 mg dose of each formulation with a 7-day washout period between doses. Sequential blood samples are withdrawn for up to 12 hours after dosing. Plasma is collected from each blood sample and is analyzed by a gas chromatographic method.

The bioavailability results obtained indicate that the bendroflumethiazide from the combination tablet is bioequivalent to bendroflumethiazide solution.

What is claimed is:

1. A solid substantially dry water-free bendroflumethiazide-containing formulation, having excellent disintegration and dissolution properties, comprising one or more excipients and a dry granulation including one or more fillers, and a preformed partial coprecipitate comprised of bendroflumethiazide, and a bendroflumethiazide wetting agent to convert said bendroflumethiazide into a more hydrophilic form, said preformed partial coprecipitate and filler being substantially homogeneously mixed with said one or more excipients.

2. The formulation as defined in claim 1 wherein said wetting agent is polyvinyl pyrrolidone, hydroxypropylmethyl cellulose, hydroxypropyl cellulose or methyl cellulose.

3. The formulation as defined in claim 1 wherein said one or more fillers comprises lactose, starch, microcrystalline cellulose, calcium phosphate, sodium starch glycolate, dicalcium phosphate or mixtures thereof.

4. The formulation as defined in claim 3 wherein said one or more fillers comprise a mixture of lactose and starch and optionally microcrystalline cellulose.

5. The formulation as defined in claim 1 in the form of a compressed tablet and said excipients include a disintegrant and lubricant, and, optionally, a colorant.

6. The formulation as defined in claim 5 wherein said disintegrant is sodium carboxymethyl starch, modified cellulose gum, microcrystalline cellulose, cross-linked polyvinyl pyrrolidone or mixtures thereof.

7. The formulation as defined in claim 5 wherein said lubricant is magnesium stearate, corn starch, talc, stearic acid or mixtures thereof.

8. The formulation as defined in claim 1 in the form of a compressed tablet, said excipients include sodium carboxymethyl starch and magnesium stearate, said one or more fillers include lactose, starch and optionally microcrystalline cellulose, and said wetting agent is polyvinyl pyrrolidone.

9. The formulation as defined in claim 1 wherein said bendroflumethiazide is present in an amount within the range of from about 1 to about 5% by weight of said formulation, said wetting agent is present in an amount within the range of from about 1 to about 6% by weight of said formulation and said one or more fillers are present in an amount within the range of from about 20 to about 95% by weight of said formulation.

10. The formulation as defined in claim 1 wherein said bendroflumethiazide is present in an amount within the range of from about 2.5 to about 10% by weight of said preformed partial coprecipitate, said wetting agent is present in an amount within the range of from about 2 to about 6% by weight of said preformed partial coprecipitate, and said one or more fillers are present in an amount within the range of from about 10 to about 90% by weight of said preformed partial coprecipitate.

11. The formulation as defined in claim 1 wherein said excipients are present in an amount within the range of from about 90 to about 98.5% by weight of said formulation.

12. The formulation as defined in claim 1 further including an anti-hypertensive compound.

13. The formulation as defined in claim 1 further including a beta-blocking compound.

14. The formulation as defined in claim 13 wherein said beta-blocking compound is nadolol.

15. The formulation as defined in claim 13 wherein said beta-blocking compound is propranolol.

16. The formulation as defined in claim 14 wherein said nadolol is present in the form of a preformed granulation including a filler.

17. A method for preparing a solid substantially dry water-free bendroflumethiazide-containing formulation as defined in claim 1, which comprises forming a wet granulation of said bendroflumethiazide including one or more fillers, a bendroflumethiazide wetting agent, and a solvent for said bendroflumethiazide, drying said wet granulation to evaporate said solvent therefrom and form a partial coprecipitate of said bendroflumethiazide and wetting agent, thereby forming a dry granulation, and mixing said dry granulation with excipients to form said solid bendroflumethiazide-containing formulation.

18. The method as defined in claim 17 further including the step of compressing said solid bendroflumethiazide-containing formulation into tablets.

19. The method as defined in claim 17 wherein said wet granulation is formed by mixing bendroflumethiazide and fillers to form a bendroflumethiazide composition, separately dissolving said wetting agent in said solvent to form a granulating mixture, and mixing said granulating mixture with said bendroflumethiazide composition.

20. The method as defined in claim 17 including the step of reducing the average particle size of said dry granulation to below about 500 microns prior to mixing same with excipients.

21. The method as defined in claim 17 further including the step of mixing said dry granulation containing bendroflumethiazide with a preformed granulation containing an anti-hypertensive agent.

22. The method as defined in claim 17 further including the step of mixing said dry granulation containing bendroflumethiazide with a preformed granulation containing a beta-blocking compound.

23. The method as defined in claim 22 wherein said beta-blocking compound is nadolol.

24. The method as defined in claim 22 wherein said beta-blocking compound is propranolol.

* * * * *